United States Patent [19]

Evers et al.

[11] 3,958,029
[45] May 18, 1976

[54] NOVEL FLAVORING COMPOSITIONS AND PRODUCTS COMPRISING 2,5-DIMETHYL-3-THIOISOVALERYL FURAN

[75] Inventors: William J. Evers, Red Bank; Howard H. Heinsohn, Jr., Hazlet; Bernard J. Mayers, Cliffwood Beach; Elizabeth A. Karoll, Old Bridge, all of N.J.

[73] Assignee: International Flavors & Fragrances Inc., New York, N.Y.

[22] Filed: Aug. 12, 1975

[21] Appl. No.: 603,990

Related U.S. Application Data

[63] Continuation-in-part of Ser. No. 478,369, June 11, 1974, Pat. No. 3,917,869, which is a continuation-in-part of Ser. No. 386,451, Aug. 7, 1973, Pat. No. 3,873,731.

[52] U.S. Cl. .................................................. 426/535
[51] Int. Cl.² ........................................... A23L 1/226
[58] Field of Search ..................... 260/347.2, 332.2; 426/535

[56] References Cited
UNITED STATES PATENTS 3,666,495  5/1972  Evers ................................. 426/535
3,873,731  3/1975  Evers et al. ........................ 426/535
3,917,869  11/1975  Evers et al. ........................ 426/535

FOREIGN PATENTS OR APPLICATIONS 1,283,912  8/1972  United Kingdom ................. 426/535

Primary Examiner—Joseph M. Golian
Attorney, Agent, or Firm—Arthur L. Liberman; Harold Haidt

[57] ABSTRACT

Methods for altering, modifying or enhancing the creamy, cocoa aroma and/or taste of foodstuffs comprising incorporating with such foodstuffs a small but effective amount of 2,5-dimethyl-3-thioisovaleryl furan having the structure:

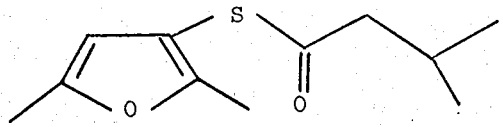

6 Claims, No Drawings

NOVEL FLAVORING COMPOSITIONS AND PRODUCTS COMPRISING 2,5-DIMETHYL-3-THIOISOVALERYL FURAN

This application is a continuation-in-part of application for U.S. Pat. No. 478,369 filed on June 11, 1974 (U.S. Pat. No. 3,917,869, issued on Nov. 4,, 1975), which, in turn, is a continuation-in-part of application for U.S. Pat. No. 386,451 filed on Aug. 7, 1973 (now U.S. Pat. No. 3,873,731).

BACKGROUND OF THE INVENTION

The present invention provides methods for altering, modifying or enhancing the creamy, cocoa aroma and/or taste of foodstuffs by adding to such foodstuffs quantities of 2,5-dimethyl-3-thioisovaleryl furan and it further relates to compositions adapted to alter, modify or enhance the creamy, cocoa aroma and/or taste of foodstuffs.

There is a need for materials which can impart a desired flavor and/or aroma to foodstuffs or which can be used to enhance or alter the naturally occurring flavors in foodstuffs. Chocolate- and cocoa-flavored foodstuffs are very popular, and a great deal of effort has gone into the preparation of materials which have a natural chocolate or cocoa flavor and into efforts to improve the chocolate and cocoa flavors of certain types of natural materials.

In the past, it was found that substitute chocolate and cocoa flavoring materials lacked certain flavor and aroma characteristics found in quantity chocolate and cocoa, and the products made from such materials were deficient in such characteristics.

U.S. Pat. No. 3,666,495 provided materials having certain desirable meat, roast meat and roasted fragrance and flavor notes. Such materials are organic oxygen containing heterocyclics wherein the second carbon atom from the oxygen atom contains a sulfur substituent and included 3-thia furan compounds having the structure:

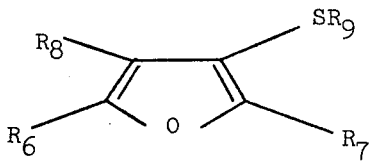

wherein $R_6$, $R_7$, $R_8$ and $R_9$ are the same or different alkyl or hydrogen. The process disclosed in that patent indicated that such furan 3-thiols and alkyl substituted furan 3-thiols can be produced by the reaction of an appropriate dihydro furanone-3-or tetrahydro furanone-3-with hydrogen sulfide in the presence of anhydrous hydrogen chloride at temperatures of −60°C to −100°C.

South African Patent No. 69/4539 dated June 26, 1969 discloses, fr use as intermediates for subsequent reaction with hydrogen sulfide to form flavor compounds, dihydro furyl thioesters having the structure:

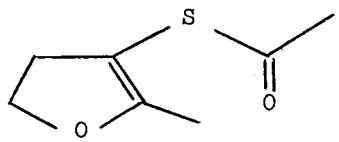

and

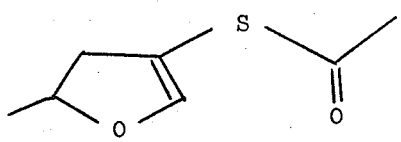

See pages 6 and 7 of the said South African Patent.

Volume 24 "Food Technology" page 535 (May, 1970) (the "Gras IV" list No. 3162) discloses the use as a flavor adjuvant furfural thioacetate having the structure:

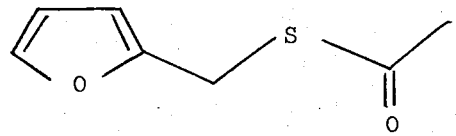

Nothing in the prior art, however, sets forth implicitly or explicitly the 2,5-dimethyl-3-thioisovaleryl furan of our invention and its unique and advantageous and unobvious flavor properties.

THE INVENTION

Briefly, this invention provides 2,5-dimethyl-3-thioisovaleryl furan which is capable of imparting a creamy, cocoa flavor and/or aroma or of enhancing such flavor and aroma, or modifying such flavor and aroma, depending upon the environment of use of said 2,5-dimethyl-3-thioisovaleryl furan. The present invention also provides flavoring compositions and food compositions containing small quantities of such 2,5-dimethyl-3-thioisovaleryl furan effective to impart a creamy, cocoa flavor and/or fragrance quality to, or enhance such quality in, such compositions or modify or alter such quality in such compositions.

Many chocolate and cocoa foods and flavoring materials lack a certain flavor and aroma note, and this lack substantially detracts from their overall organoleptic impression. It has been found that one of these missing flavor notes is one which can be characterized as creamy, cocoa-like. This creamy, cocoa-like flavor and aroma note is supplied to chocolate, cocoa and other flavors according to the present invention by the addition of 2,5-dimethyl-3-thioisovaleryl furan having the structure

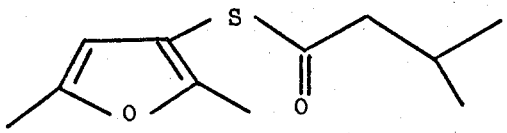

In many instances the optimum balance of flavor and/or aroma is obtained by utilizing a mixture of 2,5-dimethyl-3-thioisovaleryl furan and, in addition, phenyl alkenals, which are described in the following patents:
U.S. Pat. No. 3,582,360
U.S. Pat. No. 3,754,038
U.S. Pat. No. 3,694,232
U.S. Pat. No. 3,829,504.

When mixtures of 2,5-dimethyl-3-thioisovaleryl furan and these aldehydes are used their proportions can be varied to suit the particular composition which is to be flavored, enhanced, or otherwise altered and will depend upon whether the invention is being utilized to enhance the flavor of a chocolate, cocoa, or other foodstuff which already has some desirable flavor and aroma characteristics or whether the entire flavor and/or aroma are to be supplied by the addition of a flavoring composition. For example, it has been found when preparing cocoa flavors that a good blend is obtained by using a mixture of about 30–40% 2,5-dimethyl-3-thioisovaleryl furan; 40–50% of 5-methyl-2-phenyl-2-hexenal, about 3–7% of 4-methyl-2-phenyl-2-pentenal and from about 3–7% of 2-phenyl-2-butenal. It will be understood that these ratios can be varied as necessary to enhance or fortify the flavor of the foodstuff. All parts, proportions, percentages and ratios herein are by weight, unless otherwise indicated.

It will thus be appreciated from the foregoing that the 2,5-dimethyl-3-thioisovaleryl furan according to this invention can be mixed with other flavoring ingredients, carriers, and vehicles to form flavoring compositions suitable for imparting a flavor to, enhancing the flavor in, or altering or modifying the flavor of, a food composition, that is an edible composition.

The 2,5-dimethyl-3-thioisovaleryl furan according to this invention can also be added directly to a food composition to alter, enhance, modify or impart flavor to the food composition. In the latter instance it is only necessary to add the 2,5-dimethyl-3-thioisovaleryl furan and to make certain that it is thoroughly and uniformly distributed through the food.

The terms "alter" and "modify" in their various forms are used herein to mean the supplying or imparting of a flavor or aroma characteristic or note to an edible substance, or augmenting an existing flavor or aroma characteristic where the natural flavor or intrinsic odor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note.

When the 2,5-dimethyl-3-thioisovaleryl furan of this invention is used in flavoring compositions to enhance existing flavors in, or to provide the entire flavor impression to, a foodstuff, the 2,5-dimethyl-3-thioisovaleryl furan can be combined with organic acids including fatty, saturated, unsaturated and amino acids, alcohols including primary and secondary alcohols, esters, carbonyl compounds including aldehydes and ketones, lactones, cyclic organic materials including benzene derivatives, alicyclics, heterocyclics such as furans, pyridines, pyrazines and the like, sulfur-containing materials including thiols, sulfides, disulfides and the like, proteins, lipids, carbohydrates, and so-called flavor potentiators such as mono sodium glutamate, guanylates, inosinates, natural flavoring materials such as cocoa, vanilla, artificial flavoring materials such as vanillin, and the like. It will be appreciated that the types and amounts of materials selected from the foregoing groups of materials will depend upon the precise organoleptic character desired in the finished product and, especially in the case of flavoring compositions used to enhance other flavors, will vary according to the foodstuff to which flavor and aroma are to be imparted. Inorganic materials such as sodium chloride and freshness preservers such as butylated hydroxyanisole and propyl gallate can be added for their adjuvant or preservative effects on the flavoring composition.

As noted above, it can also be desirable to utilize carriers such as gum arabic and carrageenen or vehicles such as ethyl alcohol, water, or propylene glycol. When the carrier is an emulsion, the flavoring composition can also contain emulsifiers such as mono- and diglycerides of fatty acids and the like. With these carriers or vehicles the desired physical form of the composition can be prepared. It will be understood that the 2,5-dimethyl-3-thioisovaleryl furan of this invention can be used in spray-dried, liquid, encapsulated, emulsified and other forms in which flavorings are added to foodstuffs. The 2,5-dimethyl-3-thioisovaleryl furan can be so used alone or in combination with the other ingredients set forth herein. In the case of a foodstuff which is prepared from a combination of ingredients, the 2,5-dimethyl-3-thioisovaleryl furan flavor enhancers and flavoring compositions of this invention can be added to one of the ingredients and thereby be incorporated into the composition as a whole.

The amount of 2,5-dimethyl-3-thioisovaleryl furan used should be sufficient to impart a creamy, cocoa flavor and aroma note to the ultimate foodstuff in which the 2,5-dimethyl-3-thioisovaleryl furan is used. Thus, a small but effective amount of 2,5-dimethyl-3-thioisovaleryl furan sufficient to provide a creamy cocoa flavor note to round out the cocoa, chocolate, or other flavor note in the ultimate foodstuff is used. The amount used will vary depending upon the ultimate food composition to be flavored; for example, more may be required in providing a full, rounded chocolate flavor to an unflavored material and less may be required when this invention is used to enhance a chocolate or cocoa foodstuff or flavoring material which is deficient in natural flavor or aroma.

Those skilled in the art will appreciate that the amount of 2,5-dimethyl-3-thioisovaleryl furan can be varied over a range to provide the desired flavor and aroma. The use of too little of the 2,5-dimethyl-3-thioisovaleryl furan according to this invention will not give the full benefit, while too much of the 2,5-dimethyl-3-thioisovaleryl furan will make the flavor compositions and foodstuffs needlessly costly, and in extreme cases, will unbalance the flavor and aroma so that optimum results are not obtained.

It is accordingly preferred that the ultimate food composition contain at least about 50 parts per billion (ppb) of the 2,5-dimethyl-3-thioisovaleryl furan based on total composition, and it is not generally desirable to use more than about 500 ppm (parts per million) in the finished composition. Accordingly, the desirable range for use in the practice of this invention is from about 80 ppb to about 500 ppm of the 2,5-dimethyl-3-thioisovaleryl furan. When 2,5-dimethyl-3-thioisovaleryl furan is added to the foodstuff in the form of chocolate, cocoa, or other flavor composition, the amount should be sufficient to impart the requisite flavor and/or aroma note to the composition so that the flavor and aroma will be balanced in the finished foodstuff. Accordingly, the flavoring compositions of this invention preferably contain from about 0.002 to about 10% of the 2,5-dimethyl-3-thioisovaleryl furan.

The 2,5-dimethyl-3-thioisovaleryl furan according to this invention is added to the foodstuff either alone or as flavor compositions formed by admixture of this 2,5-dimethyl-3-thioisovaleryl furan with conventional chocolate, cocoa, or other "heavy" flavor and aroma ingredients such as the phenyl alkenals of U.S. Patents:

U.S. Pat. No. 3,582,360
U.S. Pat. No. 3,754,038
U.S. Pat. No. 3,694,232
U.S. Pat. No. 3,829,504;

and/or amyl phenyl acetate, vanillin, n-butyl phenyl ethyl acetal and diacetyl. These can be combined in proportions normally used in the art for preparation of the flavor. For example:

| | |
|---|---|
| Amylphenyl acetate | 4.000 oz. av. |
| Vanillin | 4.000 oz. av. |
| Aldehyde $C_{18}$ | 0.125 oz. av. |
| Veratraldehyde | 0.125 oz. av. |
| n-Butylphenyl ethylacetal | 0.500 oz. av. |
| Propylene glycol 3 lb., | 0.250 oz. av. |
| Diacetyl | 0.500 oz. av. |
| 5-Methyl 2-phenyl 2-hexenal | 0.500 oz. av. |
| 2,5-dimethyl-3-thioisovaleryl furan | 0.500 oz. av. |
| Total: 3lb., 10.5 oz. | |

When the 2,5-dimethyl-3-thioisovaleryl furan according to this invention is used in the formulation of chocolate flavoring material, it has been found especially useful to combine it with a vanilla flavoring agent and an alkyl acetate. Thus, the 2,5-dimethyl-3-thioisovaleryl furan can be combined with vanilla extract or other vanilla flavoring agent such as vanillin and with amyl phenyl acetate. Compositions containing 2,5-dimethyl-3-thioisovaleryl furan according to this invention with vanillin and the amyl phenyl acetate provide a flavor enhancer which imparts a more natural cocoa flavor and aroma to imitation cocoa flavor compositions.

The flavoring compositions of this invention can be added to the foodstuffs by conventional methods known in the art. For example, in the preparation of a chocolate frosting mix, the flavoring compositions can be incorporated with the fat, sugar, thickeners, freshness, preservers and the like, and admixed in a conventional blender to obtain the desired consistency. Alternatively, the flavor material of this invention, together with any other liquids if desired, can be admixed with a carrier, such as gum arabic, gum tragacanth, carrageenen and the like, and spray-dried to obtain a particulate solid flavoring material.

Where a powdered prepared cocoa mix is being made, the dried milk solids, sugar and flavoring compositions or 2,5-dimethyl-3-thioisovaleryl furan of this invention are mixed together, in a dry blender to attain uniformity. In the case of such prepared dry mixes, the 2,5-dimethyl-3-thioisovaleryl furan or flavor compositions of the present invention can be distributed on one or more of the solid ingredients or any portion thereof, for example the dried milk solids, and subsequently blended with the other ingredients.

When liquid materials are involved in the preparation of foodstuffs, for example, cake batter and chocolate milk, the flavoring materials of this invention can be combined with either the liquid to be used in the finished composition, or alternatively they can be added with a liquid carrier in which they are dissolved, emulsified, or otherwise dispersed.

The 2,5-dimethyl-3-thioisovaleryl furan of this invention can be prepared by means of the following general reaction sequence:

i. providing a 2-ene-1,4-dione having the structure:

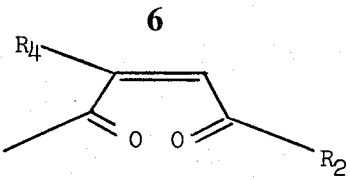

ii. intimately admixing said 2-ene-1,4dione with a thio acid having the formula $R_3SH$ thereby providing a substituted or unsubstituted 2-thia substituted 1,4 dione having the structure:

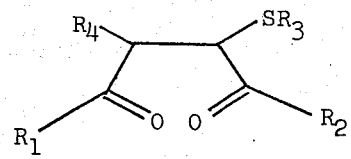

iii. cyclizing said 2-thia-substituted-1,4-dione to form a substituted or unsubstituted 3-thia furan having the formula:

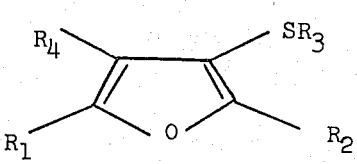

iv. optionally, when $R_3$ is not isovaleryl hydrolyzing the 3-thia furan to form a 3-mercapto furan having the structure:

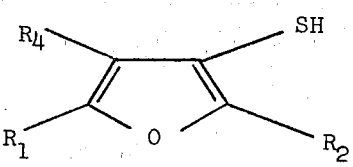

v. reacting the thus formed 3-mercapto furan with an acylating or aroylating agent thus forming a new acyl or aroyl 3-thia furan having the structure:

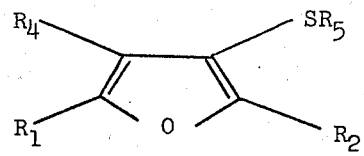

wherein $R_1$ and $R_2$ are each methyl; wherein $R_4$ is hydrogen; wherein $R_3$ is acyl or aroyl, e.g. isovaleryl; and wherein $R_5$ is isovaleryl, different from $R_3$.

The foregoing process is described in detail in the following U.S. Patents:

| | |
|---|---|
| Serial Number 478,368 | Allowed May 1, 1975 (U.S. Pat. No. 3,922,288, issued on Nov. 25, 1975 |
| Serial Number 386,453 | Patent 3,872,111 March 18, 1975 |
| Serial Number 478,328 | Issue Fee paid June 26, 1975 (U.S. Pat. No. 3,910,966, issued on Oct. 7, 1975) |
| Serial Number 386,451 | Patent 3,873,731 March 25, 1975 |
| Serial Number 478,369 | POL 85, June 13, 1975 |

-continued
(U.S. Pat. No. 3,917,869,
(U.S. Pat. No. 3,917,869,
issued on Nov. 4, 1975).

The following examples II–VIII are given to illustrate embodiments of the invention as it is preferably preferred to practice it. It will be understood that these examples are illustrative and the invention is not to be considered as restricted thereto except as indicated in the appended claims.

EXAMPLE I

Preparation of 2,5-Dimethyl-3-Thioisovaleryl Furan

A. Preparation of Cis-3-hexene-2,5-dione

In a 1000 ml round bottom flask fitted with condenser and magnetic stirrer are placed 200 g of 2,5-dimethoxy-2,5-dimethyl-2,5-dihydrofuran and 200 ml of a 1% aqueous acetic acid solution. The resulting solution is heated to reflux, refluxed for 2 minutes, cooled with an ice bath to 25°C and 625 ml of a 2% sodium bicarbonate solution is added. The solution is saturated by addition of 23 g of sodium chloride and extracted with methylene chloride (1 × 200 ml and 3 × 100 ml). After drying over sodium sulfate removal of the methylene choride in vacuo gives 142 g of crude cis-3-hexene-2,5-dione which by GLC analysis is about 90% product having the structure:

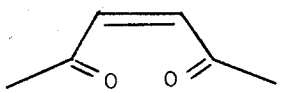

B. Preparation of 3-Thioacetyl-2,5-hexanedione

In a 1000 ml round bottom flask fitted with magnetic stirrer, thermometer, addition funnel and reflux condenser are placed 142 g of crude cis-3-hexene-2,5-dione (ex Part A), 380 ml of ether and five drops of piperidine. Thio acetic acid (96.6 g) is added over a period of 1 hour. When about one-eighth of the thio acetic acid is added the solution begins to reflux which continues during the remainder of the addition. After addition is complete the mixture is allowed to stand for 85 minutes. Ether is then removed in vacuo (water aspirator) to give 235 g of crude material containing about 91% 3-thioacetyl-2,5-hexanedione. Distillation of a 134 g portion of the crude gives 84.5 g of 3-thioacetyl-2,5-hexanedione boiling at 86 to 87°C at 0.5 torr. NMR, IR and mass spectral analysis confirm the structure:

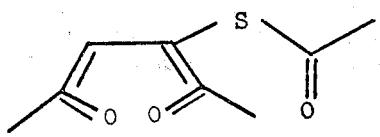

C. Preparation of 2,5-Dimethyl-3-thioacetyl furan using isopropenyl acetate

In a 500 ml three necked round bottom flask fitted with reflux condenser, thermometer, mechanical stirrer and addition funnel is placed 225 ml of isopropenyl acetate. The isopropenyl acetate is heated to reflux and 0.5 ml of concentrated sulfuric acid is added. A solution of 25 g of 3-thioacetyl furan (produced according to Part B) in 25 ml of isopropenyl acetate is added over a 20 minute period while maintaining reflux. The mixture is heated at reflux for an additional 20 minutes and then cooled to room temperature during which time 10 g of sodium bicarbonate is added. After removal of isopropenyl acetate in vacuo (35° at 20 mm), 50 ml of benzene is then added and the mixture is placed in a separatory funnel. 10 ml of water is then added to the mixture, and when carbon dioxide evolution stops, the aqueous layer is separate. Concentration in vacuo (35° bath, 20 mm) of the organic phase gives 22.2 g of a dark brown oil. Distillation of the oil gives 16.5 g of 2,5-dimethyl-3-thioacetyl furan boiling at 47° to 48°C at 0.25 mm.

D. Preparation of 2,5-Dimethyl-3-furanthiol

In a 1000 ml, three-necked flask fitted with thermometer, reflux condenser, nitrogen inlet and mechanical stirrer is placed 35 g of 2,5-dimethyl-3-thioacetyl furan (produced by the process of Part C) and 350 ml of 15% sodium hydroxide solution. The two phase mixture is heated to reflux and after 35 minutes becomes homogeneous. The mixture is heated another 20 minutes and cooled to room temperature. The pH of the solution is adjusted to 1 by the addition of 310 ml of 20% sulfuric acid and the resulting mixture extracted with ether (3 × 100 ml). Washing of the combined ether solutions with saturated sodium chloride solution (4 × 75 ml), drying with anhydrous sodium sulfate and solvent removal in vacuo (25°C at 55 mm) gives 26.2 g of crude material. Distillation of the crude material gives 17.3 g of 2,5-dimethyl-3-furanthiol boiling at 79°C at 43 mm. MS, NMR and IR analysis confirm the material as 2,5-dimethyl-3-furanthiol.

E. Preparation of 2,5-dimethyl-3-thioisovaleryl furan

Into a 25 ml flask equipped with magnetic stirrer, thermometer and addition funnel, are added:

| | |
|---|---|
| (i) 2,5-dimethyl-3-furan thiol | 1.0 g |
| (produced according to Part D) | (0.0078 moles) |
| (ii) Diethyl ether | 10 ml |

After stirring for five minutes, 0.62 g pyridine (0.0078 moles) is added to the reaction mass. After the pyridine addition, 0.94 g of isovaleryl chloride (0.0078 moles) is added, dropwise, from the addition funnel, over a 2-minute period, to the reaction mass. A white precipitate forms which is pyridine hydrochloride. The temperature in the flask rises to 35°C. After stirring for a 30 minute period, the reaction mass is filtered via suction filtration, and the filtrate is concentrated in vacuo, to a yellow-orange liquid (containing a small amount of solid) weighing 1.56 g. The major peak is trapped out by GLC and analyzed via mass spectral, NMR and IR analysis. It is confirmed to be 2,5-dimethyl-3-thioisovaleryl furan having the structure:

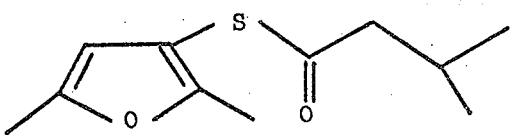

Mass Spectral Analysis:
Molecular Ion, then in decreasing intensity: 212, 57, 128, 93, 85, 212, 127 m/e
NMR Analysis (CDCl$_3$):

| Signal | Interpretation |
|---|---|
| 0.97 (d, 6) | —CH(CH$_3$)(CH$_3$) |
| 2.17 (s, 3) | |
| 2.22 (s, 3) | furan ring with H$_3$C and CH$_3$ |
| 2.45 (m, 2) | >CH$_2$ |
| 5.84 (s, 1) ppm | —H |

EXAMPLE II

The following formulation is prepared (butter flavor formulation):

| Ingredient | Parts by Weight |
|---|---|
| Diacetyl | 60.000 |
| Butyric acid | 250.000 |
| Caproic acid | 37.000 |
| Caprylic acid | 17.000 |
| 2,5-Dimethyl-3-thioisovaleryl furan (prepared according to the process of Example I) | 0.004 |
| Acetyl propionyl | 2.500 |
| Methyl nonyl ketone | 0.100 |
| Cyclotene | 20.000 |
| Delta decalactone | 205.000 |
| Delta dodecalactone | 408.396 |

The 2,5-dimethyl-3-thioisovaleryl furan in the above butter flavor composition at 0.004% adds a sweet creaminess to the butter fulness. Flavoring margarine at 0.04% and approximately the same for baked products puts this application at 1 to 3 parts per million.

EXAMPLE III

In Royal instant vanilla pudding (ingredients: sugar and dextrose, precooked starch, sodium and calcium phosphates, salt, vegetable shortening, artificial flavor and color, vegetable monoglycerides, butylated hydroxy anisole, butylated hydroxy toluene, citric acid and corn oil; produced by Standard Brands, Inc., New York, N.Y.) at 80 parts per billion (.008 grams of 0.1% dilution of 2,5-dimethyl-3-thioisovaleryl furan in 100 grams of pudding) a panel evaluation (5 panelists) was performed. The panel of five agreed that the pudding was much sweeter with no off character than such pudding without the said 2,5-dimethyl-3-thioisovaleryl furan. The panel of five also agreed that the general over-all aroma of the said pudding was enhanced as compared with the same pudding without the 2,5-dimethyl-3-thioisovaleryl furan.

EXAMPLE IV

The following formulation is prepared (butter flavor formulation):

| Ingredient | Parts by Weight |
|---|---|
| Diacetyl | 60.000 |
| Butyric acid | 250.000 |
| Caproic acid | 37.000 |
| Caprylic acid | 17.000 |
| 2,5-Dimethyl-3-thioisovaleryl furan prepared according to Example I | 0.004 |
| Acetyl propionyl | 2.500 |
| Methyl nonyl ketone | 0.100 |
| Cyclotene | 20.000 |
| Delta decalactone | 205.000 |
| Delta dodecalactone | 408.396 |

The 2,5-dimethyl-3-thioisovaleryl furan in the above butter flavor composition at 0.004% adds a sweet creaminess to the butter fullness. Flavoring margarine at 0.04% and approximately the same for baked products puts this application at 1 to 3 parts per billion.

EXAMPLE V

A panel evaluation similar to that carried out in Example III was carried out on Royal instant chocolate pudding containing 2,5-dimethyl-3-thioisovaleryl furan at a level of 80 parts per billion. The five panelists agreed that the 2,5-dimethyl-3-thioisovaleryl furan has a definite blending and rounding off effect on the pudding flavor. In addition, two of the panelists thought that the 2,5-dimethyl-3-thioisovaleryl furan deepened the character of the cocoa itself and all five panelists agreed that the 2,5-dimethyl-3-thioisovaleryl furan improved the general flavor character of the chocolate pudding as compared to the same chocolate pudding without said 2,5-dimethyl-3-thioisovaleryl furan.

EXAMPLE VI

The following base cocoa flavor material is prepared by admixing the following ingredients:

| Ingredient | Parts |
|---|---|
| Vanillin | 60.0 |
| Amyl phenyl acetate | 45.0 |
| Benzyl butyrate | 2.5 |
| Veratraldehyde | 2.5 |
| Maltol | 1.0 |
| Propylene glycol | 530.0 | to 1 g of this base cocoa flavor, 50 mg of 5-methyl-2-phenyl-2-hexenal and 20 mg of 2,5-dimethyl-3-thioisovaleryl furan are added. The addition of these two materials alters the imitation cocoa flavor to provide a more natural cocoa flavor and impart a character of "bitter-sweet" chocolate.

EXAMPLE VII

To 100 ml of sweetened milk, 100 mg of the base cocoa flavor material described in Example VI is added. The same is divided into two equal portions. To one portion 2 mg of 5-methyl-2-phenyl-2-hexenal and 2 mg of 2,5-dimethyl-3-thioisovaleryl furan are added. The portion with added 2,5-dimethyl-3-thioisovaleryl furan and hexenal has a good flavor resembling genuine chocolate milk more closely than the portion to which no such mixture is added.

What is claimed is:

1. A process for preparing a food composition which comprises adding to a food a small but effective amount of 2,5-dimethyl-3-thioisovaleryl furan to impart a creamy, cocoa-like flavor to the composition.

2. A process according to claim 1 wherein in addition to the 2,5-dimethyl-3-thioisovaleryl furan there is also added to the food a phenyl alkenal selected from the group consisting of 5-methyl-2-phenyl-2-hexenal, 4-methyl-2-phenyl-2-pentenal and 2-phenyl-2-butenal, the proportion of 2,5-dimethyl-3-thioisovaleryl furan:-phenyl alkenal being from 2:5 up to 1:1.

3. A food composition which comprises a food and an amount of 2,5-dimethyl-3-thioisovaleryl furan sufficient to impart a creamy, cocoa-like flavor quality to the composition.

4. A food composition according to claim 3 wherein there is also present at least one phenyl alkenal selected from the group consisting of 5-methyl-2-phenyl-2-hexenal, 4-methyl-2-phenyl-2-pentenal and 2-phenyl-2-butenal, the proportion of 2,5-dimethyl-3-thioisovaleryl furan:phenyl alkenal being from 2:5 up to 1:1.

5. A composition for altering, modifying or enhancing the creamy, cocoa-like flavor of a foodstuff comprising:
   i. From about 0.002% up to about 10% by weight of said composition of 2,5-dimethyl-3-thioisovaleryl furan; and
   ii. At least one additional flavoring agent selected from the group consisting of:
   Amylphenyl acetate;
   Vanillin;
   Veratraldehyde;
   n-Butylphenyl ethylacetal;
   Diacetyl;
   5-Methyl-2-phenyl-2-hexenal;
   4-Methyl-2-phenyl-2-pentenal;
   2-phenyl-2-butenal;
   Maltol;
   Benzyl butyrate;
   Butyric acid;
   Caproic acid;
   Caprylic acid;
   Acetyl propionyl;
   Methyl nonyl ketone;
   Cyclotene;
   Delta decalactone; and
   Delta dodecalactone;

6. The food flavoring composition of claim 5 comprising an additional ingredient, a carrier.

* * * * *

UNITED STATES PATENT AND TRADEMARK OFFICE
CERTIFICATE OF CORRECTION

PATENT NO. : 3,958,029

DATED : May 18, 1976

INVENTOR(S) : William J. Evers; Howard H. Heinsohn, Jr.; Bernard J. Mayers; Elizabeth A. Karoll It is certified that error appears in the above—identified patent and that said Letters Patent are hereby corrected as shown below:

Col. 1, line 59, third word, "fr" should be --- for ---

Col. 3, line 23, "2,5-d imethyl" should be --- 2,5-dimethyl ---

Col. 8, line 11, fourth word, "separate." should be --- separated. ---

Signed and Sealed this

Twenty-eighth Day of September 1976

[SEAL]

Attest:

RUTH C. MASON
*Attesting Officer*

C. MARSHALL DANN
*Commissioner of Patents and Trademarks*